(12) United States Patent
Mueller et al.

(10) Patent No.: US 7,173,715 B2
(45) Date of Patent: ***Feb. 6, 2007

(54) REDUCED COHERENCE SYMMETRIC GRAZING INCIDENCE DIFFERENTIAL INTERFEROMETER

(75) Inventors: Dieter Mueller, Cupertino, CA (US); Rainer Schierle, Los Altos, CA (US); Daniel Kavaldjiev, Santa Clara, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/157,341

(22) Filed: Jul. 12, 2005

(65) Prior Publication Data

US 2006/0126076 A1    Jun. 15, 2006

Related U.S. Application Data

(63) Continuation of application No. 09/543,604, filed on Apr. 5, 2000, now Pat. No. 7,057,741, which is a continuation-in-part of application No. 09/335,673, filed on Jun. 18, 1999, now Pat. No. 6,414,752.

(51) Int. Cl.
*G01B 9/02* (2006.01)
(52) U.S. Cl. ............... 356/503; 356/521; 356/514
(58) Field of Classification Search ........... 356/497, 356/503, 511–514, 521
See application file for complete search history.

(56) References Cited

U.S. PATENT DOCUMENTS

| | | | |
|---|---|---|---|
| 3,090,279 A | 5/1963 | Chisolm | |
| 3,614,235 A | 10/1971 | Munnerlyn | |
| 3,726,595 A | 4/1973 | Maysumoto | |
| 3,891,321 A | 6/1975 | Hock | |
| 4,537,508 A | 8/1985 | Doyle | |
| 5,000,542 A | 3/1991 | Nishimura et al. | |
| 5,050,993 A | 9/1991 | Tansey | |
| 5,196,902 A | 3/1993 | Solomon | |
| 5,249,032 A | 9/1993 | Matsui et al. | |
| 5,268,742 A | 12/1993 | Magner | |
| 5,392,113 A | 2/1995 | Sayka et al. | |

(Continued)

FOREIGN PATENT DOCUMENTS

DE            261422            10/1988

(Continued)

*Primary Examiner*—Hwa (Andrew) Lee
(74) *Attorney, Agent, or Firm*—Smyrski Law Group, A P.C.

(57) ABSTRACT

A system for inspecting specimens such as semiconductor wafers is provided. The system provides scanning of dual-sided specimens using a diffraction grating that widens and passes nth order (n>0) wave fronts to the specimen surface and a reflective surface for each channel of the light beam. Two channels and two reflective surfaces are preferably employed, and the wavefronts are combined using a second diffraction grating and passed to a camera system having a desired aspect ratio. The system preferably comprises a damping arrangement which filters unwanted acoustic and seismic vibration, including an optics arrangement which scans a first portion of the specimen and a translation or rotation arrangement for translating or rotating the specimen to a position where the optics arrangement can scan the remaining portion(s) of the specimen. The system further includes means for stitching scans together, providing for smaller and less expensive optical elements.

20 Claims, 9 Drawing Sheets

U.S. PATENT DOCUMENTS

| | | |
|---|---|---|
| 5,471,303 A | 11/1995 | Ai et al. |
| 5,485,272 A | 1/1996 | Dirksen et al. |
| 5,526,116 A | 6/1996 | de Groot |
| 5,541,729 A | 7/1996 | Takeuchi et al. |
| 5,574,560 A | 11/1996 | Franz et al. |
| 5,654,798 A | 8/1997 | Bruning |
| 5,719,676 A | 2/1998 | Kulawiec |
| 5,737,081 A | 4/1998 | Freischlad |
| 5,754,295 A | 5/1998 | Mitchell |
| 5,889,591 A | 3/1999 | Bruning |
| 5,923,425 A | 7/1999 | Dewa et al. |
| 5,943,133 A | 8/1999 | Zeylikovich et al. |
| 5,995,224 A | 11/1999 | de Groot |
| 6,075,598 A | 6/2000 | Kauppinen |
| 6,100,977 A | 8/2000 | Muller |
| 6,226,092 B1 | 5/2001 | de Lega |
| 6,249,351 B1 | 6/2001 | de Groot |
| 6,252,665 B1 | 6/2001 | Williams et al. |
| 6,407,815 B2 | 6/2002 | Akihiro |
| 6,501,552 B1 | 12/2002 | Mizuno |
| 6,535,290 B1 | 3/2003 | Spanner et al. |

FOREIGN PATENT DOCUMENTS

| | | |
|---|---|---|
| DE | 19511926 | 10/1996 |
| EP | 0575095 | 12/1993 |
| JP | 57182604 | 11/1982 |
| JP | 61023902 | 2/1986 |
| JP | 07260419 | 10/1995 |
| WO | 9825105 | 6/1998 |

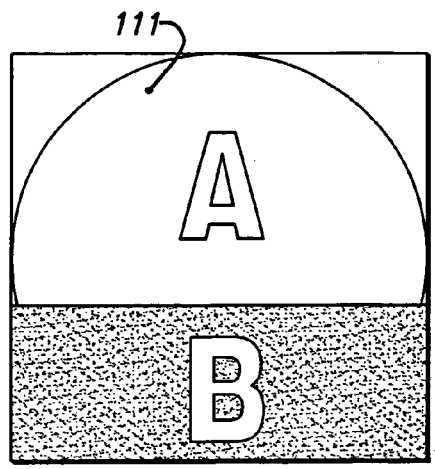
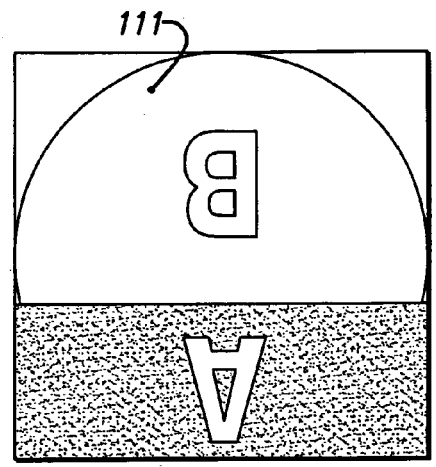
FIG. 4A          FIG. 4B
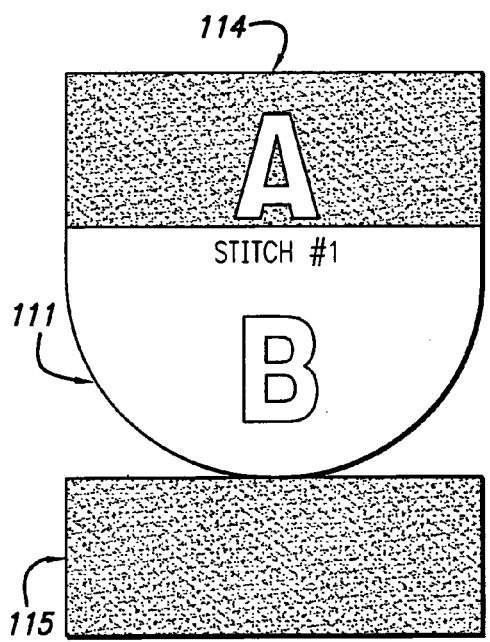
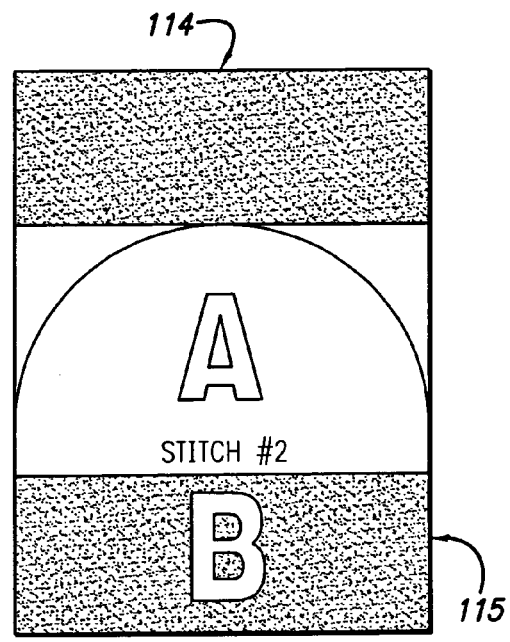
FIG. 5A          FIG. 5B

REDUCED COHERENCE SYMMETRIC GRAZING INCIDENCE DIFFERENTIAL INTERFEROMETER

This application is a continuation of U.S. patent application Ser. No. 09/519,604, entitled "Reduced Coherence Symmetric Grazing Incidence Differential Interferometer," filed Apr. 5, 2000, now U.S. Pat. No. 7,057,741 which is a continuation in part of U.S patent application Ser. No. 09/95,673, entitled "Method and Apparatus for Scanning, Stitching and Damping Measurements of a Double-Sided Inspection Tool," filed on Jun. 18, 1999, now U.S. Pat. No. 6,174,752, both of which are hereby incorporated by reference.

BACKGROUND OF THE INVENTION

1. Field of the Invention

The present invention relates generally to the field of optical imaging and more particularly to systems for sub-aperture data imaging of double sided interferometric specimens, such as semiconductor wafers.

2. Description of the Related Art

The progress of the semiconductor industry over the last years has resulted in a sharp increase in the diameters of semiconductor wafers as base material for chip production for economic and process technical reasons. Wafers having diameters of 200 and 300 millimeters are currently processed as a matter of course.

At present manufacturers and processors of wafers in the 200 and 300 mm range do not have a wide range of measuring devices available which enable inspection of particular geometric features, namely flatness, curvature, and thickness variation, with sufficient resolution and precision.

As scanning of specimens has improved to the sub-aperture range, the time required to perform full specimen inspection for a dual-sided specimen has also increased. Various inspection approaches have been employed, such as performing an inspection of one side of the specimen, inverting the specimen, and then inspecting the other side thereof. Such a system requires mechanically handling the specimen, which is undesirable. Further, the act of inspecting the specimen has generally required binding the specimen, which can cause deformation at the edges of the specimen, increase defects at the edge, or cause bending of the specimen during inspection.

One method for inspecting both sides of a dual sided specimen is disclosed in PCT Application PCT/EP/03881 to Dieter Mueller and currently assigned to the KLA-Tencor Corporation, the assignee of the current application. The system disclosed therein uses a phase shifting interferometric design which facilitates the simultaneous topography measurement of both sides of a specimen, such as a semiconductor wafer, as well as the thickness variation of the wafer. A simplified drawing of the Mueller grazing incidence interferometer design is illustrated in FIG. 1A. The system of FIG. 1A uses a collimated laser light source 101 along with a lens arrangement 102 to cause grazing of light energy off the surface of both sides of the specimen 103 simultaneously. A second lens arrangement 104 then provides focusing of the resultant light energy and a detector 105 provides for detection of the light energy.

The design of FIG. 1A is highly useful in performing topographical measurements for both sides of a dual-sided specimen in a single measurement cycle, but suffers from some drawbacks. First, the system requires minimum specimen movement during measurement, which can be difficult due to vibration in the surrounding area and vibration of the specimen itself. Further, the inspection can be time consuming and requires highly precise light energy application and lensing, which is expensive. The specimen must be free standing and free of edge forces, and the incidence geometry during inspection must be unimpeded. Illumination access must be preserved under all incidence angles. These factors provide mechanical challenges for successfully supporting the specimen; excessive application of force at a minimum number of points may deform the specimen, while numerous contact points impede access and require exact positioning to avoid specimen deformation or bending during inspection. Further, edge support of the specimen has a tendency to cause the specimen to act like a membrane and induce vibration due to slight acoustic or seismic disturbances. This membrane tendency combined with the other problems noted above have generally been addressed by including most components of the system within an enclosure that minimizes ambient vibrations, which adds significant cost to the system and does not fully solve all vibration problems.

Further, the previous system has a tendency to require excessive coherence lengths. As is generally known in the art, the coherence length is the distance along the emitted laser beam over which the laser light has sufficient coherence to produce visible interference fringes. Coherence length is important when a laser beam is split and recombined to form an interference pattern, as in the system presented in FIG. 1A.

In general, when a laser beam is split, the optical path difference is the difference in length between the two paths before recombining. If the optical path difference is less than the longitudinal spatial coherence length of the light beam, interference fringes are formed at the receiving element, or screen. If the optical path difference is greater than the longitudinal spatial coherence length, no interference fringes form. Thus it is desirable to have a small spatial coherence length to minimize the size of the components involved.

The system of FIG. 1A provides a high spatial coherence between the reference wave fronts and the specimen wave fronts. Such a system makes the overall measurement system highly sensitive to background noise along the optical path. The noise creates a diffraction pattern on top of the measurement signal and thus degrades the image obtained of the surfaces. In particular, the background signal tends to be unstable and can be difficult to correct using compensation techniques.

The cost of lenses sized to accommodate inspection of a full wafer in the arrangement shown in FIG. 1A is significant, and such lenses generally have the same diameter as the diameter of the specimen, on the order of 200 or 300 millimeters depending on the application. Full aperture decollimating optics, including precision lenses, gratings, and beamsplitters used in a configuration for performing full inspection of a 300 millimeter specimen are extremely expensive, generally costing orders of magnitude more than optical components half the diameter of the wafer.

Further, the system disclosed in FIG. 1A requires a high spatial coherence between the reference wave fronts and the specimen wave fronts, making the system sensitive to background noise along the optical path. Noise creates a diffraction pattern that increases the measurement signal in a random fashion. The result unstable and compensation for the combined effect is extremely difficult.

It is an object of the current system to provide a system having a relatively small spatial coherence length to minimize system sensitivity to background noise along the optical path and permit use of reasonably sized enclosure components.

It is another object of the current invention to provide a system for performing a single measurement cycle inspection of a dual-sided specimen having dimensions up to and greater than 300 millimeters.

It is a further object of the present invention to provide a system for inspection of dual-sided specimens without requiring an excessive number of binding points and simultaneously allowing free access for inspection of both sides of the specimen.

It is a further object of the current invention to provide for the single measurement cycle inspection of a dual-sided specimen while minimizing the tendency for the specimen to behave as a membrane and minimize any acoustic and/or seismic vibrations associated with the inspection apparatus and process.

It is still a further object of the present invention to accomplish all of the aforesaid objectives at a relatively low cost, particularly in connection with the collimating and decollimating optics and any enclosures required to minimize acoustic and seismic vibrations.

SUMMARY OF THE INVENTION

The present invention is a system for inspecting a wafer, including inspecting both sides of a dual sided wafer or specimen. The wafer is mounted using a fixed three point mounting arrangement that holds the wafer at a relatively fixed position while simultaneously minimizing bending and stress. Light energy is transmitted through a lens arrangement employing lenses having diameter smaller than the specimen, such as half the size of the specimen, arranged to cause light energy to strike the surface of the wafer and subsequently pass through second collimating lens where detection and observation is performed.

The inventive system includes a variable coherence light source that transmits light energy through a collimator, which splits the light energy into two channels and directs said light energy to a diffraction grating. The diffraction grating splits each of the two beams into two separate first order beams, or a total of four first order beams. Two of these first order beams are directed to the wafer surface, while the other two are directed toward flat reflective surfaces facing the wafer surfaces. Another diffraction grating is positioned to receive The four first order beams and combine said beams into two separate channels, each of which are directed to a separate camera. Each camera is specially designed to receive the signal provided and resolve the image of the wafer surface.

In an alternate arrangement, the system includes at least one light source mounted proximate and substantially parallel to a flat in the arrangement previously described. The purpose of this optional source is to provide a catadioptric inspection of the surface. The light source, such as a helium-neon laser, passes through a beamsplitter, through a collimator, through the flat and strikes the wafer surface. The light beam then reflects off the wafer surface, passes through the flat, through the collimator, is deflected by the beamsplitter, and is received by a camera element or other sensing device.

The system optionally employs a calibration object for distortion calibration needed to match the front side and back side images of the wafer to determine the thickness variation of the wafer.

The system preferably includes at least one damping bar, where the number of damping bars depends on the wafer repositioning arrangement. The effect of the damping bar is to perform viscous film damping, or VFD, of the non-measured surface of the specimen to minimize the effects of vibration in accordance with VFD, or the Bernoulli principle. Each damping bar is positioned to be within close proximity of the surface to be damped. The proximity between any damping bar and the surface of the wafer is preferably less than 0.5 millimeters, and spacing of 0.25 and 0.33 may be successfully employed. Smaller gaps provide problems when warped specimens are inspected. One embodiment of the current invention employs a damping bar to cover slightly less than half of the specimen when in scanning position.

Mounting for the wafer uses a three point kinematic mount. The mounting points include clips having spherical or semi-spherical tangentially mounted contacts, mounted to a support plate and arranged to be substantially coplanar, where the clips are adjustable to provide for slight irregularities in the shape of the wafer. The adjustability of the contact points provide the ability to hold the wafer without a stiff or hard connection, which could cause bending or deformation, as well as without a loose or insecure connection, which could cause inaccurate measurements.

A wafer or specimen to be measured is held on a holding device such that both plane surfaces are arranged in vertical direction parallel to the light beam P. The wafer is supported substantially at its vertical edge so that both surfaces are not substantially contacted by the support post and are freely accessible to the interferometric measurement.

In the preferred configuration, a translation surface or mounting surface holds the contact points and the wafer or specimen is fastened to a translation stage, which provides translation or sliding of the specimen within and into the lensing/imaging arrangement. The system first performs an inspection of one portion of the specimen, and the translation stage and wafer are repositioned or translated such as by driving the translating stage so that another portion of the wafer is within the imaging path. The other portion of the wafer is then imaged, and both two sided images of the wafer are "stitched" together. Optionally, more than two scans may be performed and stitched together. The number of scans relates to the size of the wafer and the collimators and cameras used. Smaller components tend to be less costly, and thus while performing more than one scan may introduce stitching errors and require additional time to perform a scan of the entire surface, such a system may be significantly less expensive.

Other means for presenting the remaining portion of wafer or specimen may be employed, such as rotating the wafer mechanically or manually, or keeping the wafer fixed and moving the optics and imaging components. Alternately, scanning may be performed using multiple two-sided inspections of the module, such as three, four, or five or more scans of approximate thirds, quarters, or fifths, and so forth of the specimen. While multiple scans require additional time and thus suffer from increased throughput, such an implementation could provide for use of smaller optics, thereby saving overall system costs.

In a two phase scan of a dual sided specimen, at least 50 percent of the surface must be scanned in each phase of the scan. It is actually preferred to scan more than 50 percent, such as 55 percent, in each scan to provide for a comparison between scans and the ability to "stitch" the two scans together.

Scanning and stitching involves determining the piston and tilt of the specimen during each scan, adjusting each scan for the piston and tilt of said scan, and possibly performing an additional stitching procedure. Additional stitching procedures include, but are not limited to, curve fitting the points between the overlapping portions of the two scans using a curve fitting process, replacing overlapping pixels with the average of both data sets, or weighting the averaging in the overlapping region to remove edge transitions by using a trapezoidal function, half cosine function, or other similar mathematical function. Background references are preferably subtracted to improve the stitching result. If significant matching between the scans is unnecessary, such as in the case of investigating for relatively large defects, simply correcting for tilt and piston may provide an acceptable result. However, in most circumstances, some type of curve fitting or scan matching is preferred, if not entirely necessary.

These and other objects and advantages of the present invention will become apparent to those skilled in the art from the following detailed description of the invention and the accompanying drawings.

DESCRIPTION OF THE DRAWINGS

FIG. 4A shows the first position of the wafer or specimen relative to a damping bar when a rotational scanning and stitching procedure is performed on approximately half the wafer surface;

FIG. 4B is the second position of the wafer or specimen relative to a damping bar when a rotational scanning and stitching procedure is performed on the other approximately half of the wafer surface;

FIG. 5A shows the first position of the wafer or specimen relative to a damping bar arrangement when a translational scanning and stitching procedure is performed on approximately half the wafer surface;

FIG. 5B is the second position of the wafer or specimen relative to a damping bar arrangement when a translational scanning and stitching procedure is performed on the other approximately half of the wafer surface;

DETAILED DESCRIPTION OF THE INVENTION

Figure 1A:
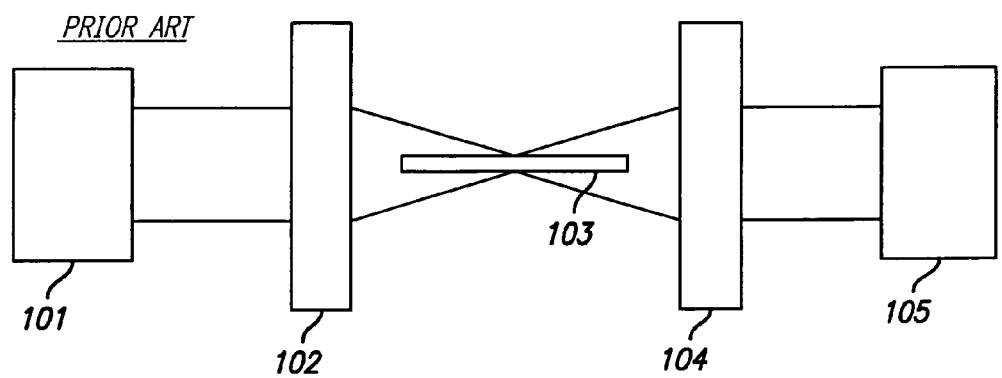
FIG. 1A illustrates the general concept of the predecessor Mueller system for inspecting both sides of a semiconductor wafer or specimen when said specimen is oriented in a substantially "vertical" orientation.
Figure 1B:
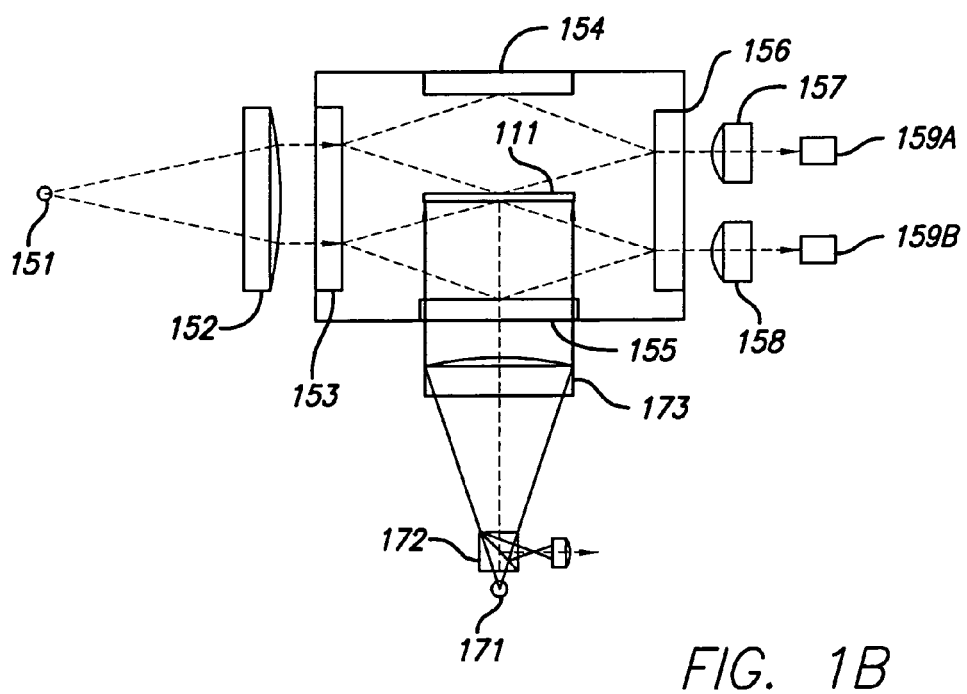
FIG. 1B is a preferred embodiment of the current invention.

FIG. 1B illustrates the reduced coherence inspection device of the current invention. According to FIG. 1B, a variable coherence light source 151 is employed. The variable coherence light source 151 may be, for example, a helium-neon laser, but generally any type of variable coherence light providing sufficient illumination characteristics for the apparatus and method described herein is acceptable. The variable coherence light source transmits light energy to collimator or collimating lens 152, which directs the light to first diffraction grating 153. The collimator 152 divides the light energy into two separate channels. First diffraction grating 153 widens the nth order (n>0) wave fronts of the light energy and directs the widened light energy toward the specimen being examined. As shown in FIG. 1B, light energy is directed toward the specimen and a pair of flat reflecting surfaces 154 and 155, where the flat reflecting surfaces may have either opaque characteristics, such as a standard mirror surface, or be semi transparent, i.e. transparent through one side and <90% reflective on the other. The dotted lines representing the waveform illustrated in FIG. 1 represent the higher order, such as first order, components of the light energy passing through the diffraction grating 153. The use of a zero order blocking surface (not shown) may be included in the system to prevent passage of the zero order component of the light energy emanating from the diffraction grating 153. The blocking surface may be any type of opaque surface, such as a light absorbing surface, dimensioned to prevent passage of zero order light components and permit those higher order components illustrated in FIG. 1B to reflect in the manner illustrated. Alternatively, a diffraction grating optimized for zero intensity of its zero order can be employed, negating the need for mechanical screens.

Light energy from each of the two channels strikes the specimen 111 and each channel further reflects off a respective flat 154 or 155. Light is thereby deflected toward the second diffraction grating 156, which combines the reflected energy received from the flat 154 or 155 and the specimen surface. Second diffraction grating 156 receives and combines the two channels of information and passes each channel of optical information through a collimator to a camera. Collimators 157 and 158 decollimate the light energy received from the second diffraction grating 156.

In the system illustrated in FIG. 1B, reference surfaces and specimen surfaces are positioned such that the reference wave fronts and specimen wave fronts travel the same path length. Phase shifting may be established by moving the reference surfaces, the diffraction gratings, or the light source. Thus the overall effect of the system illustrated in FIG. 1B is to decrease the spatial coherence between the reference wave fronts and the specimen wave fronts.

As shown in FIG. 1B, an optional interferometric normal incidence inspection device may be employed in the system described above, including a light emitting device, such as a laser 171, a beam splitter 172, and a collimator 173. The flat 155 serves as a reference surface. Light emitted from the light emitting device passes through the beam splitter toward the collimator, which collimates the light beam and passes it through the, in this case, semi transparent, flat 155 and toward the specimen 111. Light then reflects from the surface of the specimen 111 and from the reflective surface of the flat 155 facing the specimen, through the flat 155, through the collimator 173, and toward the beam splitter 172. The beam splitter 172 directs the reflected beam to supplemental collimator 174 and to a camera arrangement. This apparatus provides for an additional channel of inspection and can be combined with the illustrated two channels of information to provide additional information enhancing the quality of the scan. Further, the normal incidence arrangement may also be employed on the other side of specimen 111, providing yet further optical information of the specimen surface.

The camera system 159 comprises camera arrangement 159A and camera arrangement 159B. The camera system or anamorphic imaging system has an aspect ratio of on the order of 2:1. In essence, the wafer in the configuration illustrated optically appears as a tilted object, and in the arrangement shown has an elliptical projection ratio of approximately 6:1. The camera system used should preferably resolve this elliptical projection ratio into an image having an aspect ratio closer to 1:1. Maintaining the aspect ratio of 6:1 can prevent detection of relatively significant magnitude.

Figure 1C:
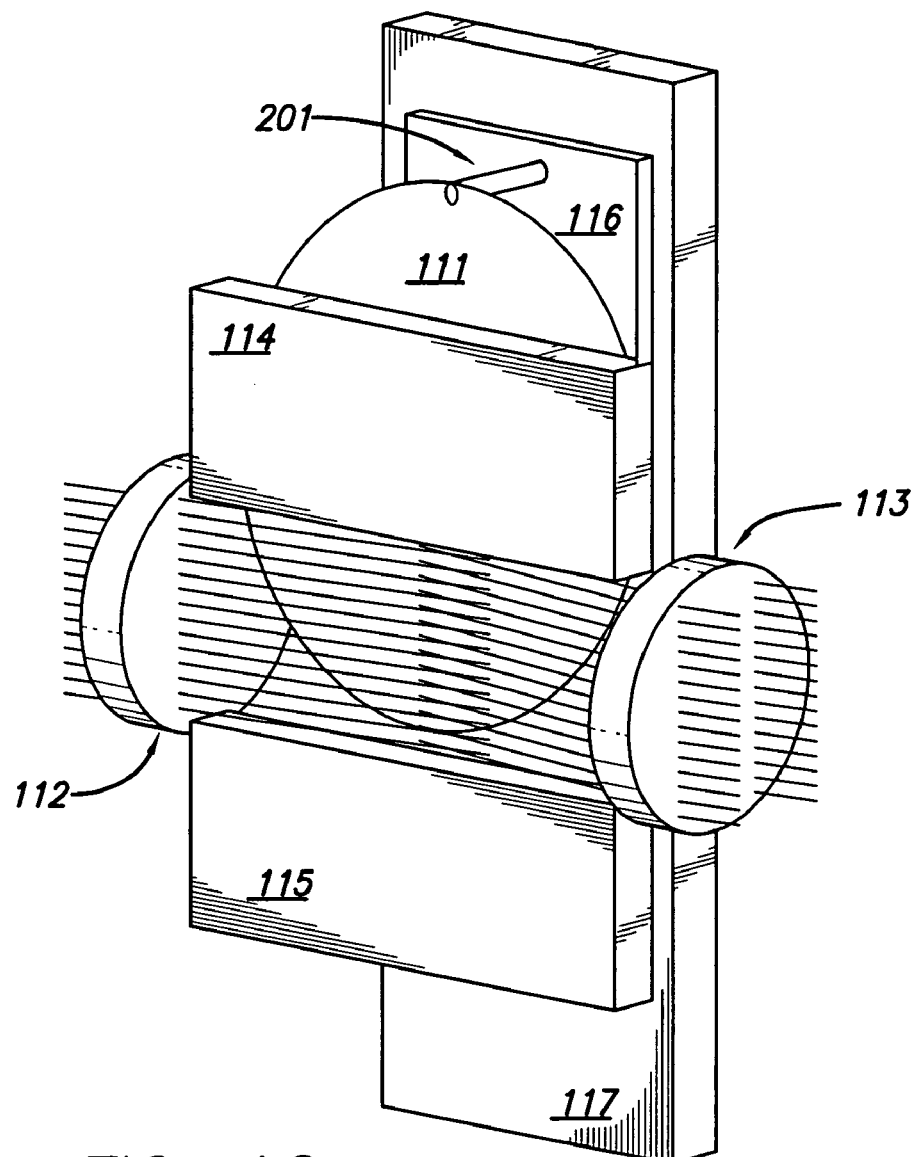
FIG. 1C illustrates a holding arrangement for use in the current invention, including a damping bar and dual sided lensing arrangement.
Figure 1D:
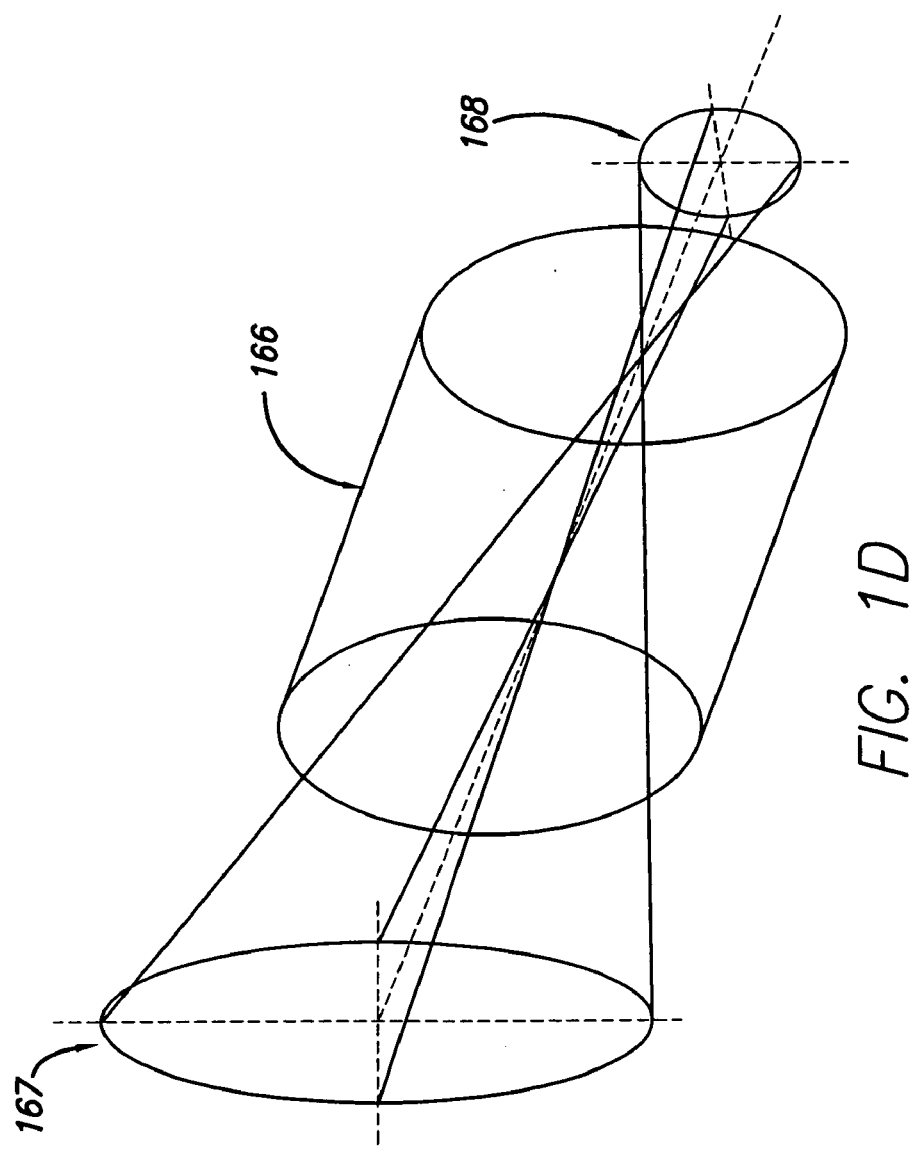
FIG. 1D is a conceptual illustration of the anamorphic imaging system used in the system disclosed herein.

The overall configuration of the anamorphic imaging system used in the system disclosed herein is shown in FIG. 1D. From FIG. 1D, the projection of the image has an elliptical aspect ratio of 6:1. The anamorphic imaging system 166 receives the elliptical image 167 and conveys the image to a viewing location, such as a CCD (Charged Coupled Device) such that the received image 168 has an aspect ratio of 2:1. This ratio provides the maximum utilization of a square image when imaging each of the wafer stitching regions. Different anamorphic imaging arrangements may be employed while still within the scope of the current invention; the intention of the anamorphic system and function thereof is to provide a sufficient image based on the surfaces being scanned and the size and quality of defects expected, as well as the resolution capability of the overall system.

Figure 1E:
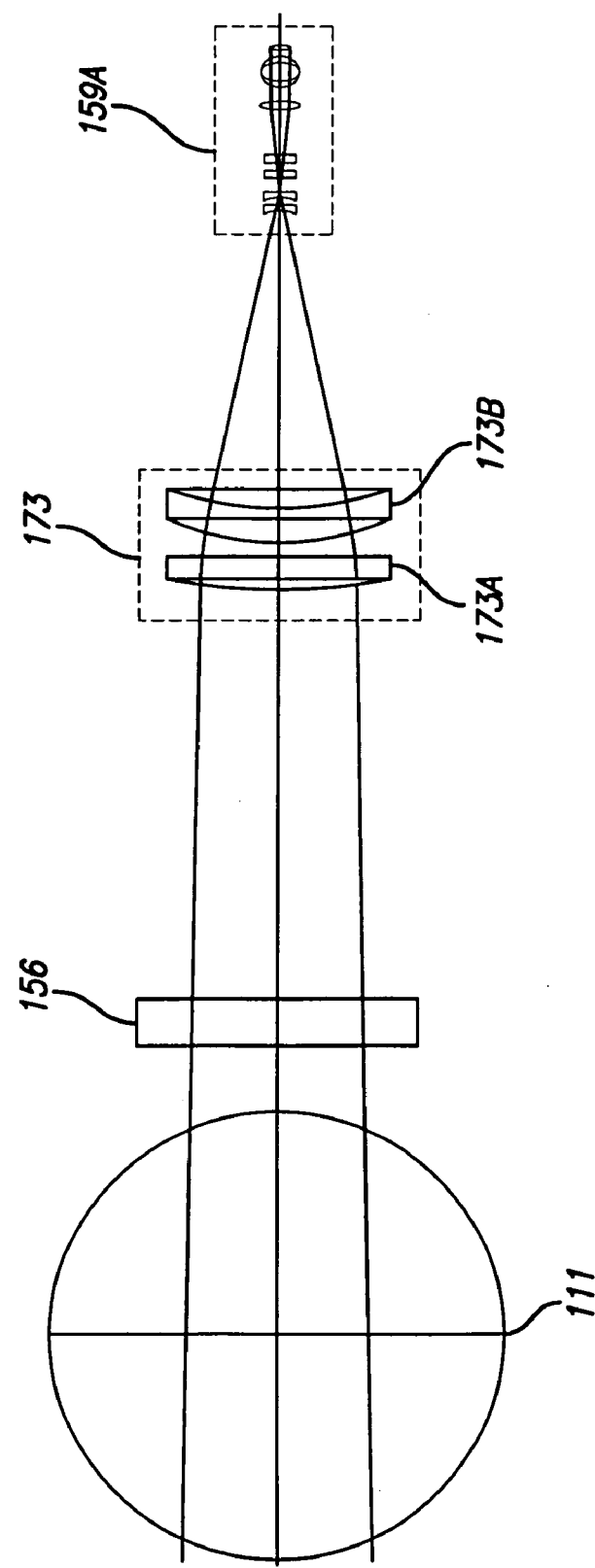
FIG. 1E shows a single channel camera system setup employed in the current system, including the optical components between the specimen or wafer and the CCD.

A simplified drawing of the system from the wafer to the camera arrangement 153 is presented in FIG. 1E. FIG. 1E is not to scale and represents a single channel of inspection rather than a dual channel and dual camera arrangement. From FIG. 1E, wafer or specimen 111 reflects the light energy toward second diffraction grating 156, which passes light to collimator 173, comprising decollimating lenses 173A and 173B, and to a camera arrangement 159A. Camera arrangement 159A comprises seven imaging lenses used to resolve the 6:1 image received into a 2:1 image for transmission to CCD 160. Any lensing arrangement capable of producing this function is acceptable, and the camera arrangement 159A is therefore not limited to that illustrated in FIG. 1E.

An additional feature of the current system is the use of a calibration object for distortion calibration. In the system illustrated, a calibration object 175 (not shown) is used in place of wafer or specimen 111. The use of a calibration object provides a known reference which enables accurate matching of images on the front and back side of the wafer 111 with sub pixel accuracy. The use of the calibration object 175 permits calculation of the thickness variation of the specimen by determining the difference between the front and back topography maps of the specimen. The calibration object is similar to a wafer having the same pattern on the front and backsides at the same coordinates. The accuracy of the calibration object features is detectable using the system/interferometer with pixel accuracy. One type of calibration object employs a symmetric pattern of circular raised features having relatively small diameters/pitches, such as on the order of 5 to 10 millimeters, and covering both the front and back surfaces. Other patterns, pitches, and spacings may be employed as long as the precision of the measuring device may be determined.

Figure 2:
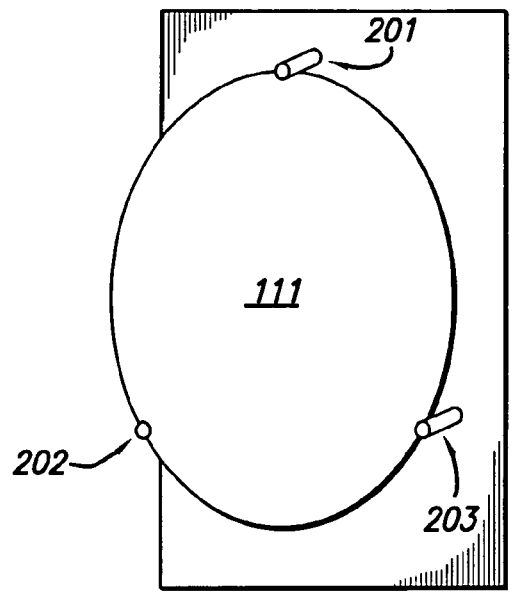
FIG. 2 presents the operation of mounting points for the wafer or specimen.

In operation, the calibration object 175 is placed as shown in FIGS. 1B and 1C and images of the front surface and back surface obtained. The features on the front and back surfaces of the calibration object are measured and their locations are determined to within the desired accuracy. A spatial transformation is computed which maps the measured locations of the features to their actual locations. The wafer or specimen 111 is positioned in the system as shown, with sufficient care taken to place the wafer or specimen 111 in an identical position to the calibration object 175. The specimen is then examined on both front and back sides and the thickness variation determined by applying the same spatial transformation as for the calibration wafer FIG. 1C illustrates scanning both sides of a dual-sided wafer or specimen 111. According to FIG. 1C, the wafer 111 is mounted using a fixed three point mounting arrangement as shown in FIG. 2. The three point mounting arrangement serves to hold the wafer 11 at a relatively fixed position while simultaneously minimizing any bending or stressing of the dual-sided wafer. Light energy is transmitted through first collimating lens 112 arranged to cause light energy to strike the surface of the wafer 111 and subsequently pass through second collimating lens 113 where detection and observation is performed. As may be appreciated by examining FIG. 1C, the diameter of both first collimating lens 112 and second collimating lens 113 are significantly smaller than the diameter of the specimen or wafer 111, and incident light strikes only a portion of the surface of wafer 111. Not shown in the illustration of FIG. 1C is that while light energy is striking the surface of wafer 111 visible in the arrangement shown, light energy simultaneously passes through first collimating lens 112 and strikes the reverse side of the wafer 111, not shown in FIG. 1C. Light energy passes from the reverse side of the specimen 111 through second collimating lens 113.

The arrangement further includes an upper damping bar 114 and a lower damping bar 115. In the arrangement shown in FIG. 1C, the upper damping bar 114 covers approximately one half of the specimen 111, specifically the half not being inspected. The effect of the damping bar is to damp the non-measured surface of the specimen 111 to minimize the effects of vibration. Damping in this arrangement is based on VFD, or the Bernoulli principle, wherein the upper damping bar 114 in the arrangement shown is brought to within close proximity of the surface to be damped. The proximity between either damping bar 114 or 115 and the surface of the wafer is preferably less than 0.5 millimeters, and spacing of 0.25 and 0.33 may be successfully employed. The problem associated with providing smaller gaps between either damping bar 114 or 115 and the surface of wafer 111 is that any warping of the wafer may cause the bar to contact the surface. For this reason, and depending on the wafer surface, gaps less than 0.10 millimeters are generally undesirable. Further, gaps greater than 1.0 millimeters do not produce a desirable damping effect, as the Bernoulli principle does not result in sufficient damping in the presence of gaps in excess of 1.0 millimeter.

The gap between the specimen 111 and upper damping bar 114 or lower damping bar 115 restricts airflow between the specimen and the damping bar and damps vibration induced in the specimen. Each damping bar is generally constructed of a stiff and heavy material, such as a solid steel member. Overall dimensions are important but not critical in that the damping bar should cover a not insignificant portion of the wafer 111. Coverage of less than 20 percent of the wafer tends to minimize the overall damping effect on the wafer, but does provide some level of damping.

The illumination of only a portion of the wafer 111 permits use of smaller lenses than previously known. In the embodiment shown in FIG. 1B, the preferred size of the first collimating lens 112 and second collimating lens 113 is. Approximately 4.4 inches where the wafer 111 is 300 millimeters in diameter. In such an arrangement, the damping bars 114 and 115 are approximately 4.5 inches wide. Length of the damping bars depends on the mode of wafer movement, as discussed below.

As shown in FIG. 2, the mounting for the wafer 111 is preferably using a three point kinematic mount, where the three points 201, 202, and 203 represent spherical or semispherical contacts tangential to one another. Points 201, 202, and 203 are small clips having spherical or semi-spherical tangentially mounted contacts, mounted to a support plate such as mounting plate 116 to be substantially coplanar, with adjustable clips to provide for slight irregularities in the shape of the wafer 111. The spherical or semispherical components should be sufficiently rigid but not excessively so, and a preferred material for these components is ruby. The adjustability of points 201, 202, and 203 provide an ability to hold the wafer 111 without a stiff or hard connection, which could cause bending or deformation, as well as without a loose or insecure connection, which could cause inaccurate measurements. In FIG. 1C, two lower kinematic mount points 202 and 203 (not shown) support the lower portion of the wafer 111, while the upper portion is supported by mount point and clip 201. The points 201, 202 and 203 are therefore stiff enough to mount the wafer or specimen 111 and prevent "rattling" but not so stiff as to distort the wafer. The spherical or semispherical contact points are generally known to those of skill in the mechanical arts, particularly those familiar with mounting and retaining semiconductor wafers. The combination of clamping in this manner with the Bernoulli damping performed by the damping bars 114 and 115 serves to minimize acoustic and seismic vibration.

Figure 7:
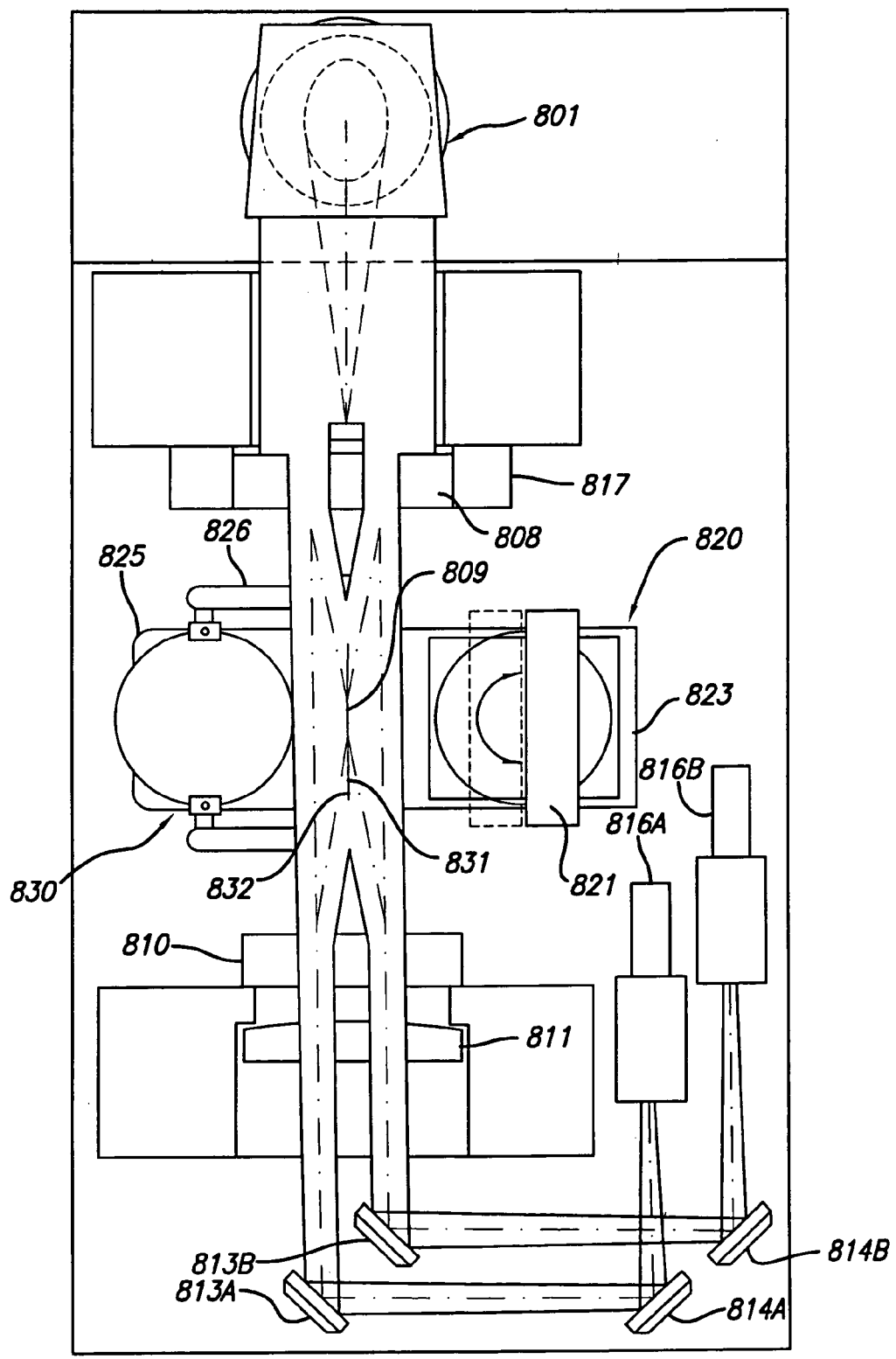
FIG. 7 presents a conceptual schematic representation of the components and optics necessary to perform the inventive dual sided imaging of a semiconductor wafer.
Figure 8:
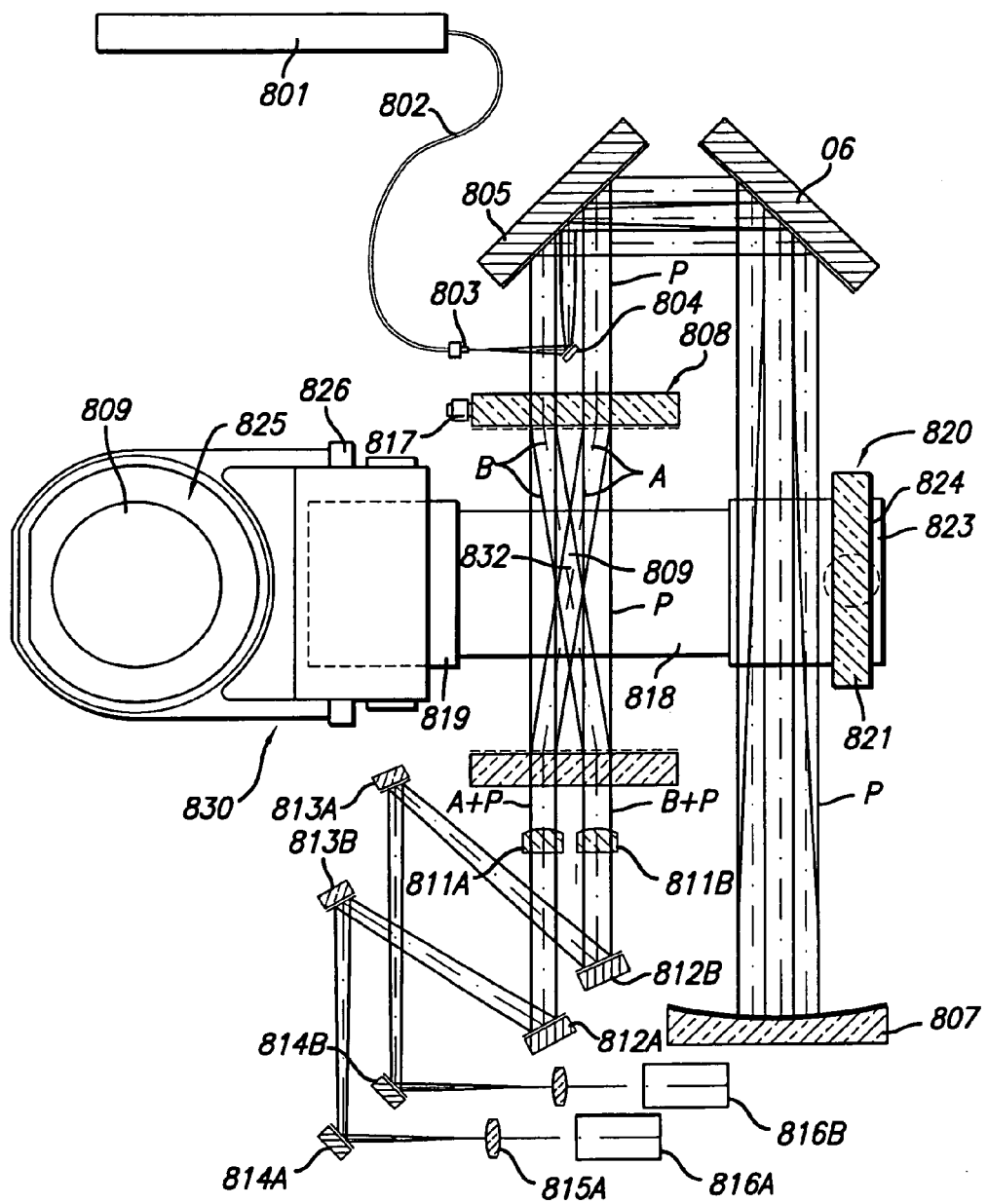
FIG. 8 is a top view of the components and optics showing the path of light energy.

Simultaneous imaging of both sides of the specimen is generally performed in accordance with PCT Application PCT/EP/03881 to Dieter Mueller, currently assigned to the KLA-Tencor Corporation, the assignee of the current application. The entirety of PCT/EP/03881 is incorporated herein by reference. This imaging arrangement is illustrated in FIGS. 7 and 8, and is employed in conjunction with the arrangement illustrated and described with respect to FIG. 1B herein. FIGS. 7 and 8, as well as FIG. 1B, are not to scale. As shown in FIGS. 7 and 8, the light energy directing apparatus employed in the current invention comprises a light source in the form of a laser 801. The light emitted from the laser 801 is conducted through a beam waveguide 802. The light produced by the laser 801 emerges at an end 803 of the beam waveguides 802 so that the end 803 acts as a punctual light source. The emerging light strikes a deviation mirror 804 wherefrom it is redirected onto a collimation mirror 807 in the form of a parabolic mirror by two further deviation mirrors 805 and 806. Deviation mirrors 805 and 806 are oriented at an angle of 90° relative to each other. The parallel light beam P reflected from the parabolic mirror 807 reaches a beam splitter 808 through the two deviation mirrors 805 and 806.

The beam splitter 808 is formed as a first diffraction grating. The beam splitter 808 is arranged in the apparatus, in a vertical direction and the parallel light beam P strikes the diffraction grating in a perpendicular direction. A beam collector 810 in the form of a second diffraction grating is disposed from the first diffraction grating 808 and parallel thereto. Behind the beam collector 810 two decollimation lenses 811 are arranged at equal level and the light beams leaving these decollimation lenses are each deflected and focused onto two CCD cameras 816A and 816B, through deviation mirror pairs 812A and 812B, 813A and 813B, and 814A and 814B, and to an optical imaging system 15.

The beam splitter 808 is supported transversely to the optical axis and further comprises a piezoelectric actuating element 817 for shifting the phase of the parallel light beam P by displacing the diffraction grating.

Figure 3:
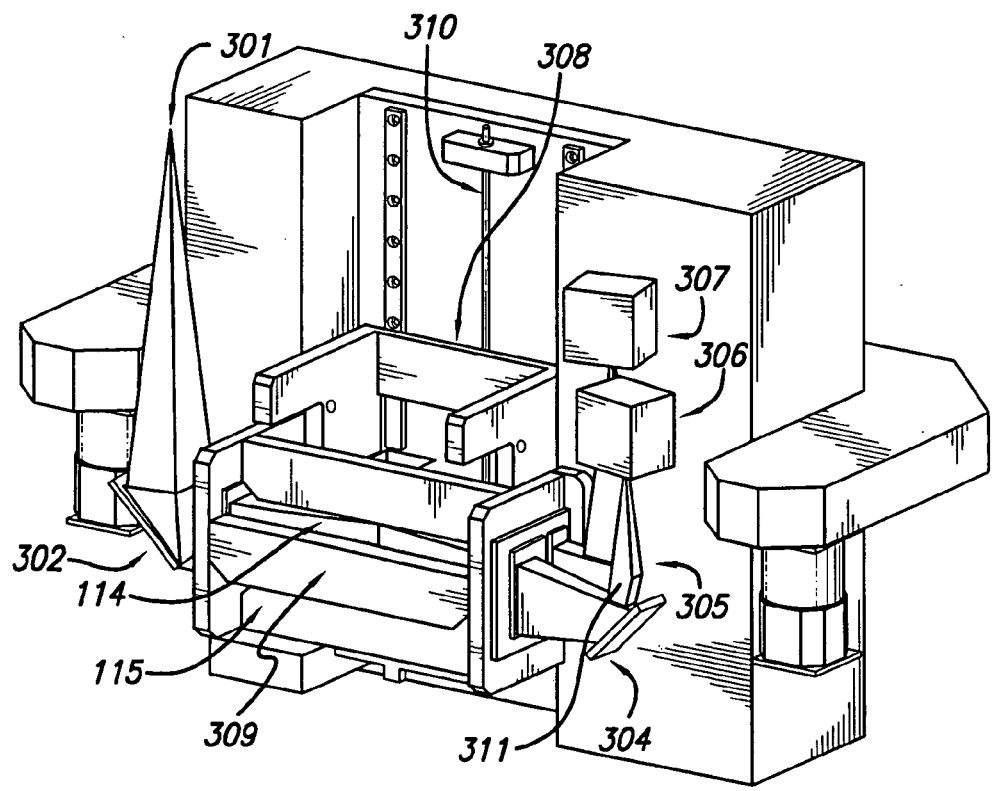
FIG. 3 illustrates a measurement module for use in connection with translating the wafer and performing multiple scans in the presence of multiple damping bars.

A holding device 830, for example the holding device disclosed herein and described with respect to FIGS. 1C, 2, and 3, is provided between the first diffraction grating and the second diffraction grating. Other holding devices may be employed while still within the scope of this invention, such as a support post. A wafer or specimen 809 to be measured is held on the holding device 830 such that both plane surfaces 831 and 832 are arranged in vertical direction parallel to the light beam P. The wafer 809 is supported by the support post substantially at its vertical edge 833 only so that both surfaces 831 and 832 are not substantially contacted by the support post and are freely accessible to the interferometric measurement.

Moreover, an optional receiving device (830, 825) may be provided for measuring the wafer 809. This receiving device (830, 825) provides for arrangement of the wafer in the system and provides an alternative to the wafer maintaining device shown in FIGS. 1C, 3, and 4. The wafer can be inserted into the receiving device in a horizontal position. By means of a tilting device 826 the wafer 809 may be tilted from its horizontal position into the vertical measuring position, and the wafer 809 may be transferred, by means of a positionable traveller, into the light path between the first diffraction grating and the second diffraction grating so that the surfaces 809 and 832 to be measured are aligned substantially parallel to the undiffracted light beam P and in a substantially vertical direction.

Furthermore, a reference apparatus 820 may be provided which comprises a reference body 821 having at least one plane surface 824. The reference body 821 can be introduced into the light path between the first diffraction grating 808 and the second diffraction grating 810 in place of the semiconductor wafer or specimen 809 to be measured by means of a traveller 823 with a linear guide 818. The reference body 821 is held so that its plane surface 824 is arranged in vertical direction parallel to the undiffracted light beam P. The reference body 821 can be turned by 180° in its mounting around an axis parallel to its surface 824.

In operation the wafer or specimen 809 to be measured is first inserted into the wafer receiving device 825. The surfaces 831 and 832 are horizontally arranged. By means of the tilting device and of the traveller 819 the wafer to be measured is brought into the holding device 830 where it is arranged so that the surfaces 831 and 832 are vertical. A diffraction of the parallel light beam P striking the first diffraction grating 808 of the beam splitter produces partial light beams A, B, whereby the first order component of the partial light beam A having a positive diffraction angle strikes the one surface 831 of the wafer 809 and is reflected thereat. The first order component of partial light beam B with a negative diffraction angle strikes the other surface 832 of the wafer and is reflected thereat. The first order component of partial light beams A and B each strike the respective flat, or mirrored surface, where the first order component of partial light beam A strikes flat 851, and first order component of partial light beam B strikes flat 852. The 0-th diffraction order of the parallel light beam P passes through the first diffraction grating 808 and is not reflected at the surfaces 831 and 832 of the wafer 809. This partial light beam P serves as references beam for interference with the reflected wave fronts of the beams A and B. Each 0-th order beam is preferably blocked by blocking surfaces 853 and 854. In the second diffraction grating 810, the beam collector and the reflected first order components of partial light beams A and B are each combined again with the reference beam P and focused, in the form of two partial light beams A+P and B+P onto the focal planes of the CCD cameras 816A and 816B through decollimation lenses 811 and deviation mirrors 812, 813 and 814 as well as positive lenses 815.

During the exposure of the surfaces the phase of the parallel light beam P is repeatedly shifted by multiples of 90° and 120° by displacing the diffraction grating. This produces phase shifted interference patterns. The defined shift of the interference phase produced by the phase shifter 817 is evaluated to determine whether there is a protuberance or a depression in the measured surfaces 831 and 832 the two digitized phase patterns are subtracted from each other.

A calibration using the reference body 821 may optionally be performed before each measurement of a wafer 809. The reference body 821 is introduced into the beam path between the first diffraction grating 808 and the second diffraction grating 810. The known plane surface 824 is measured. Subsequently the reference body 821 is turned by 180° and the same surface 824 is measured as a second surface.

FIG. 3 illustrates the measurement model without a wafer or specimen present. From FIG. 3, light source 301 initially emits light energy and is focused to strike first mirror surface 302 and second mirror surface 303 (not shown). Each of these two mirror surfaces direct light energy through first collimating lens 112 (not shown in this view) and light energy strikes the two surfaces of specimen 111 (also not shown) simultaneously. After striking the two surfaces of specimen 111, light energy is directed through second collimating lens 113 (also not shown in FIG. 2) and to third mirror 304 and fourth mirror 305, which direct light energy toward focusing element 306 and detector 307. Imaging arm 311 represents the light image path from third mirror 304 toward focusing element 306. Focusing elements and sensors are those known in the art, and may include a lensing arrangement, such as multiple lenses, and a CCD or other imaging sensor. Other implementations of focusing element 306 and detector or sensor 307 are possible white still within the scope of the current invention.

From FIG. 1C, the specimen 111 is mounted to three points, including point 201, which are fixedly mounted to mounting surface 116. Mounting surface 116 may be fixedly mounted to translation surface 117. Either translation surface 117 or mounting surface 116 is fastened to translation stage 308, which provides translation or sliding of the mounting surface 116 and specimen 111 within and into the arrangement shown in FIG. 3. The arrangement may further include translation surface 117 depending on the application. Translation stage 308 permits the arrangement of FIG. 1B, specifically wafer or specimen 111, points 201, 202, and 203, mounting surface 116, and translation surface 117, to move up and down in a relatively limited range, as described below. In such an arrangement employing translation surface 117, the translation surface and the mounting surface along with the contact points are positioned within the measurement module 300, preferably by affixing the translation surface 117 to the translation stage 308. Specimen 111 is then physically located between damping bars 114 and 115, as well as proximate damping bar 309 and fastened to points 201, 202, and 203. Once the specimen 111 has been adequately fastened to points 201, 202, and 203, an inspection of the lower portion of the wafer is initiated. After completing an adequate inspection, i.e. an inspection of one portion of the specimen 111 with acceptable results, the translation stage 308 and ultimately the wafer are repositioned or translated such as by driving the translating stage 308 along track 310 such that another portion of the wafer 111, such as the remaining approximately half of specimen 111 is within the imaging path. The other portion of the wafer is then imaged, and both of the two sided images of the wafer surface are "stitched" together.

The damping bars may have varying size while still within the scope of the current invention, as discussed above. In FIG. 3, the damping bars are affixed to end pieces 310 and 311, but any type of mounting will suffice as long as the gap spacing described above and the ability to perform scans on desired portions of the wafer is available.

As may be appreciated, other means for presenting the remaining portion of wafer or specimen 111 may be employed, such as rotating the wafer by hand by releasing contact with the points and rotating the wafer manually. Alternately, a mechanical rotation of the specimen may occur, such as by rotatably mounting the mounting surface 116 on the translating surface 117 while providing for two locking positions for the mounting surface 116. In other words, the arrangement of wafer 111, points 201, 202, and 203, and mounting surface 116 would initially fixedly engage translation surface 117. On completion of a first inspection scan of a portion of specimen 111, wafer 111, points 201, 202, and 203, and mounting surface 116 would be unlocked from translation surface 117 and be mechanically or manually rotated vertically on an axis perpendicular to translation surface 117. The wafer and associated hardware rotate 180 degrees to a second locking position, wherein the surface would lock and a second inspection scan would commence. During this rotation scheme, damping bars and impediments would be mechanically or manually removed to prevent contact with mounting points 201, 202, and 203. The various components, particularly mounting surface 116, are sized to accommodate rotation within the measurement module 300 without contacting the translation stage or other module components.

Alternately, scanning may be performed using multiple two-sided inspections of the module, such as three, four, or five scans of approximate thirds, quarters, or fifths of the specimen. While multiple scans require additional time and thus suffer from increased throughput, such an implementation could provide for use of smaller optics, thereby saving on system costs. Numerous sub-aperture scans may be performed by a system similar to that illustrated in FIG. 3 while still within the scope of the current invention.

FIGS. 4A and 4B illustrate a rotational scanning arrangement of the wafer or specimen 111. As may be appreciated, in a two phase scan of a dual sided specimen, at least 50 percent of the surface must be scanned in each phase of the scan. It is actually preferred to scan more than 50 percent, such as 55 percent, in each scan to provide for a comparison between scans and the ability to "stitch" the two scans together. In such an arrangement, as shown in FIG. 4A, over 50 percent of the surface is scanned initially, shown as portion A of the surface 111. Portion B is obscured by one of the damping bars. After the initial scan phase, the specimen 111 is rotated manually or mechanically to the position illustrated in FIG. 4B. Approximately 55 percent of the wafer surface, both front and back, are scanned during this second phase. This provides an overlap of five percent of the wafer, and comparisons between these overlap portions provides a reference for stitching the scans together. In FIG. 4B, the A portion of the wafer is obscured by the damping bar.

Alternately, as in the arrangement shown in FIG. 3, the wafer or specimen 111 may be translated vertically and two or more separate scans performed. As shown in FIGS. 5A and 5B, a portion of the wafer 111 is positioned between two damping bars, such as damping bars 114 and 115, and the portion marked "B" in FIG. 5A is scanned. As shown therein, greater than 50 percent of the specimen 111 is scanned so that the overlapping portion may be stitched with the second scan. After the initial scan, the wafer is translated to a position as shown in FIG. 5B. Portion "A" of FIG. 5B is then scanned, while the lower damping bar covers much of section. "B." The overlapping portions of the two scans are then stitched together to provide a full representation of the surface, and again such a scan is dual-sided.

From FIGS. 4A, 4B, 5A, and 5B, it should be apparent that a single damping bar is required if the specimen 111 is to be rotated as shown in FIGS. 4A and 4B, while two damping bars are required if the wafer 111 is to be translated, as shown in FIGS. 5A and 5B. Note that due to measurement setup, an arbitrary piston or DC offset and tilt will be applied to each of the measurements, indicating that some correction is required prior to or during stitching to obtain an accurate-surface representation.

Figure 6:
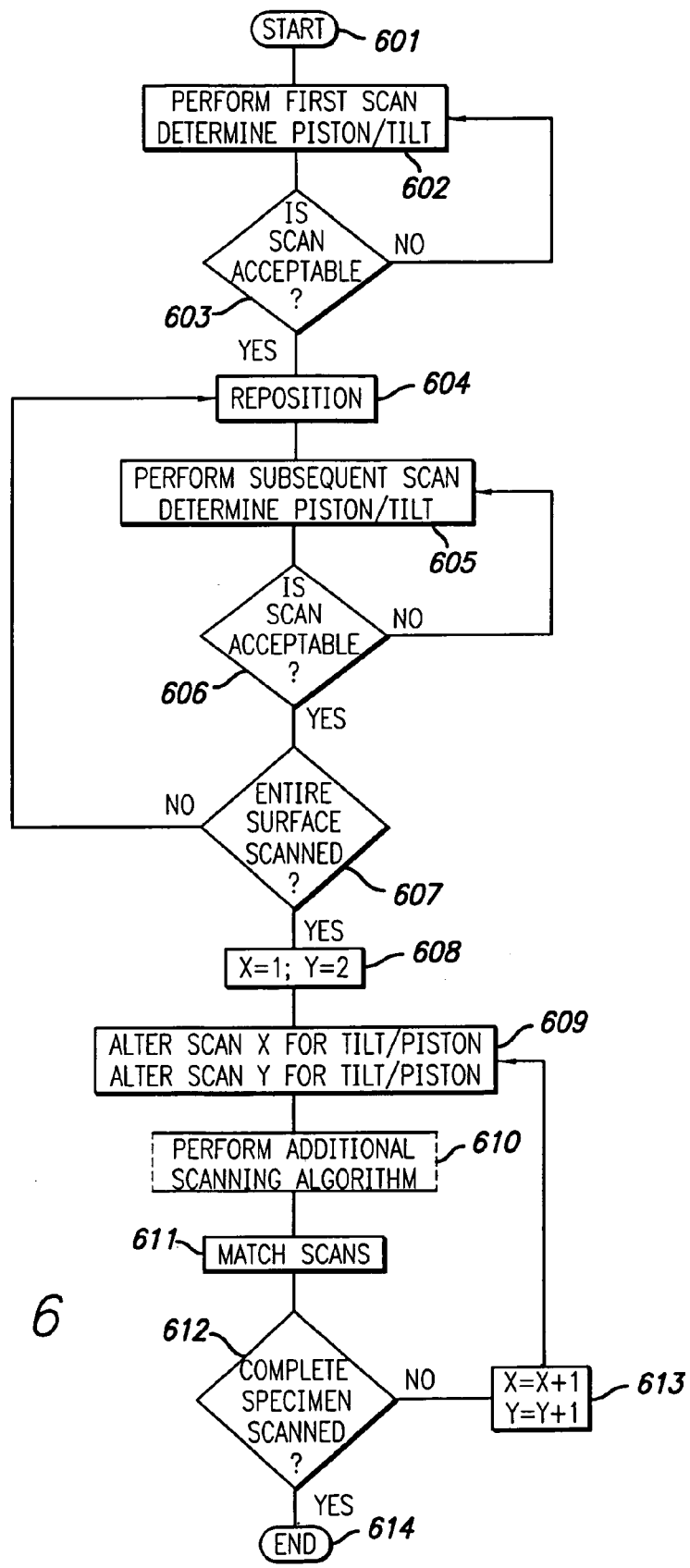
FIG. 6 represents an algorithm for performing the scanning and stitching according to the present invention.

FIG. 6 illustrates a general scanning and stitching algorithm for use in accordance with the invention described herein. The algorithm begins in step 601 and performs the first scan in step 602, as well as determining the piston and tilt of the specimen 111. The algorithm evaluates whether the scan is acceptable in step 603, either performed by an operator actually evaluating the scan or a mechanical comparison with a known or previous scan. If the scan is acceptable, the algorithm proceeds to step 604 where the wafer is repositioned to the next location. If the scan is not acceptable, the wafer is rescanned in its original position. Piston and tilt may be recomputed, but as the wafer has not moved this is not necessary. Once the wafer has been repositioned in step 604, a subsequent scan is performed in step 605 and the tilt and piston computed for the new orientation. The acceptability of the scan is evaluated in step 606, and if unacceptable, the scan performed again. The piston and tilt again do not need to be recalculated. Once the scan is mechanically or visually deemed acceptable, the algorithm determines whether the entire surface has been scanned in step 607. If the entire surface has not been scanned, the wafer is again repositioned and the remaining scans performed in accordance with the illustrated steps. If the entire surface has been scanned, the algorithm sets x equal to one and y equal to 2 in step 608. In step 609 the system alters scan x for tilt and piston and separately alters scan y for its respective tilt and piston. At this point scans x and y are neutrally positioned and may be stitched together. Step 610 is an optional step of performing an additional stitching procedure. Additional stitching procedures include, but are not limited to, curve fitting the points between the overlapping portions of the two scans using a curve fitting process, replacing overlapping pixels with the average of both data sets, or weighting the averaging in the overlapping region to remove edge transitions by using a trapezoidal function, half cosine function, or other similar mathematical function. Background references are preferably subtracted to improve the stitching result. If significant matching between the scans is unnecessary, such as in the case of investigating for relatively large defects, simply correcting for tilt and piston may provide an acceptable result, and step 610 need not be performed. However, in most circumstances, some type of curve fitting or scan matching is necessary. Scans are matched and stitched in step 611. Such stitching algorithms should preferably be performed using a computing device, such as a microprocessor (not shown).

Step 612 evaluates whether the complete wafer has been stitched together. If it has not, the algorithm proceeds to increment x and y in step 613 and perform additional stitching of the remaining portions. If the complete wafer has been stitched, the algorithm exits in step 614.

Based on the disclosure presented above and in particular in connection with that shown in FIG. 3, the wafer 111 is generally repositioned while the inspection energy source and optics remain fixed. While this implementation provides distinct advantages in setup time for performing multiple dual-sided wafer scans, it is to be understood that the light source and associated optics and detector may be sidably or rotationally mounted while the wafer remains fixed. In the configuration illustrated in FIG. 3, source 301, support elements 310 and 311, damping bars 114 and 115, damping bar 309, the four mirrors 302, 303, 304, and 305, focusing element 306, and detector 307 may be mounted to a single surface and fixedly positioned relative to one another, and translated or rotated about the wafer. Alternately, the components may be translated either together or individually to perform subsequent scans of the wafer or specimen 111.

While the invention has been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A system for measuring specimen thickness variations, comprising:
    a variable coherence light energy generating device;
    a diffraction grating arrangement for receiving uniform wavefront light energy and passing light energy toward each side of said specimen; and
    a plurality of reflective surfaces for receiving light energy from the diffraction grating arrangement, each of said reflective surfaces separate from and substantially parallel to said specimen;
    a sensor for receiving light energy from the plurality of reflective surfaces;
    wherein said variable coherence light energy generating device, said diffraction grating arrangement, and said plurality of reflective surfaces collectively interoperate to measure thickness variations for the specimen.

2. The system of claim 1, wherein each reflective surface receives nonzero order light energy passed from the diffraction grating arrangement.

3. The system of claim 1, further comprising a blocking element for blocking passage of zero order light energy received from the diffraction grating arrangement.

4. The system of claim 1, further comprising a second diffraction grating arrangement substantially matched to the diffraction grating arrangement, wherein said second diffraction grating arrangement receives light energy from said plurality of reflective surfaces and passes light energy to the sensor.

5. The system of claim 1, wherein the sensor comprises at least one camera, wherein each camera converts an elliptical image of at least one side of said specimen into an image having an aspect ratio closer to 1:1.

6. The system of claim 4, further comprising at least one collimator and at least one receiving collimator, wherein each collimator is positioned between the variable coherence light generating device and the diffraction grating arrangement and each collimator is positioned between the second diffraction grating arrangement and the sensor.

7. The system of claim 1, wherein nonzero order light energy passes from said diffraction grating arrangement toward at least one reflective surface and said specimen.

8. The system of claim 1, wherein at least one reflective surface is at least partially transparent, and said system further comprises an interferometric normal incidence inspection device positioned to operate through one at least partially transparent reflective surface.

9. The system of claim 8, wherein said interferometric normal incidence inspection device comprises a light emitting device, a beamsplitter, and a collimator.

10. The system of claim 1, wherein the diffraction grating arrangement is optimized for zero intensity of its zero order.

11. A method for measuring thickness variations of a specimen, comprising:
    transmitting relatively low coherence light energy toward said specimen;
    diffracting said low coherence light energy into multiple channels of light energy;
    directing said multiple channels of light energy toward both sides of said specimen and simultaneously to a plurality of reflective surfaces; and
    combining light energy received from both sides of the specimen.

12. The method of claim 11, wherein said diffracting comprises diffracting for zero intensity of the zero order of the multiple channels of light energy received.

13. The method of claim 11, further comprising initially calibrating the system prior to said transmitting.

14. The method of claim 11, further comprising performing an interferometric normal incidence inspection on the specimen prior to said transmitting.

15. The method of claim 11, further comprising performing an interferometric normal incidence inspection of the specimen after said directing.

16. The method of claim 11, wherein said light energy forms an image, and said directing step comprises altering the image aspect ratio.

17. An apparatus for measuring thickness variations for a specimen, comprising:
    a variable coherence energy transmitting device;
    a diffracting device for diffracting variable coherence light energy received from said variable coherence energy transmitting device toward the specimen; and
    a plurality of reflecting surfaces each oriented substantially parallel to the specimen receiving light energy from said diffracting device;
    wherein said diffracting device directs energy simultaneously toward one reflecting surface and one surface of the specimen.

18. The apparatus of claim 17, wherein said diffracting device directs said nonzero components of the variable coherence light energy toward said specimen and at least one reflecting surface.

19. The apparatus of claim 18 further comprising a blocking surface for blocking zero order components of light energy received from the diffracting device.

20. The apparatus of claim 17, further comprising a sensor arrangement, said sensor receiving an image at a first aspect ratio and configured to record said image at a second aspect ratio.

* * * * *